United States Patent
Shuchman et al.

[11] Patent Number: 5,879,304
[45] Date of Patent: Mar. 9, 1999

[54] SINGLE USE LARYNGOSCOPE BLADE

[75] Inventors: Aaron Shuchman, Ashkelon; Menachem Dvir, Hertzalia, both of Israel

[73] Assignee: Truphatek International Ltd., Netanya, Israel

[21] Appl. No.: 627,789

[22] Filed: Mar. 29, 1996

Related U.S. Application Data

[63] Continuation of Ser. No. 179,024, Jan. 7, 1994, abandoned.

[30] Foreign Application Priority Data

Nov. 12, 1993 [IL] Israel ................. 107.594

[51] Int. Cl.$^6$ ................................. A61B 1/26
[52] U.S. Cl. ........................... 600/193; 600/213
[58] Field of Search ................ 600/185, 188, 600/190, 191, 193, 195, 197, 210, 213

[56] References Cited

U.S. PATENT DOCUMENTS

| | | | |
|---|---|---|---|
| 3,426,749 | 2/1969 | Japhcott | 128/11 |
| 3,598,113 | 8/1971 | Moore | 128/11 |
| 3,766,909 | 10/1973 | Ozbey | 128/11 |
| 3,826,248 | 7/1974 | Gobels | 128/11 |
| 4,037,588 | 7/1977 | Heckele | 128/11 |
| 4,406,280 | 9/1983 | Upsher | 128/11 |
| 4,557,256 | 12/1985 | Bauman | 128/11 |
| 4,565,187 | 1/1986 | Soloway | 128/11 |
| 4,570,614 | 2/1986 | Bauman | 128/11 |
| 4,579,108 | 4/1986 | Bauman | 128/11 |
| 4,583,527 | 4/1986 | Musicant et al. | 128/11 |
| 4,596,239 | 6/1986 | Bauman | 128/11 |
| 4,679,547 | 7/1987 | Bauman | 128/10 |
| 4,878,486 | 11/1989 | Slater | 128/110 |
| 4,884,558 | 12/1989 | Gorski et al. | 128/11 |
| 4,930,495 | 6/1990 | Upsher | 128/10 |
| 4,958,624 | 9/1990 | Stone et al. | 128/11 |
| 4,972,825 | 11/1990 | Vescovo, Jr. | 128/10 |
| 5,065,738 | 11/1991 | Van Dam | 128/11 |
| 5,178,131 | 1/1993 | Upsher | 128/11 |
| 5,355,870 | 10/1994 | Lacy | 128/11 |

FOREIGN PATENT DOCUMENTS

| | | | |
|---|---|---|---|
| 0 184 588 | 6/1986 | European Pat. Off. | A61B 1/26 |
| 26 21 232 | 11/1977 | Germany | A61B 1/22 |

*Primary Examiner*—Beverly M. Flanagan
*Attorney, Agent, or Firm*—Townsend and Townsend and Crew LLP

[57] ABSTRACT

A disposable plastic laryngoscope blade is detachably connectable to a hook-on-type conventional metallic laryngoscope handle in conformity with International Standard ISO-7376-1. The blade comprises a rigid plastic housing having a lower, tongue-engaging flange section extending along the length thereof, an upper, teeth-engaging flange section, and web sections interconnecting the upper and lower flanges to form a hollow cavity; an electric bulb having a rating of about 2 to about 2.5 Volts and about 0.35 to about 0.5 Amperes, positioned within the cavity adjacent the distal end of the blade and having positive and negative electrode conductors extending therefrom; a proximal base end provided with hooks or fittings for engaging complementary handle hooks or fittings in compliance with ISO-7376-1, the proximal base being provided with a positive central contact positioned to press against a standard insulated central contact provided in the handle when attached thereto, and elevating into an operating position to maintain conductivity from a power source in the handle and ensure illumination of the bulb while in the engaged operating position; a first current-conducting means connecting the positive electrode conductor to the positive central contact and a second current-conducting means connecting the negative electric conductor with a metallic surface of the handle.

11 Claims, 2 Drawing Sheets

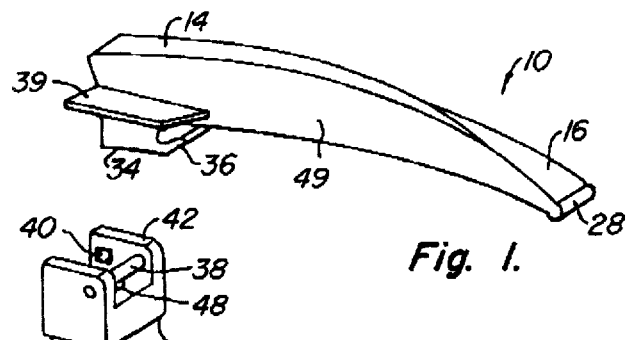
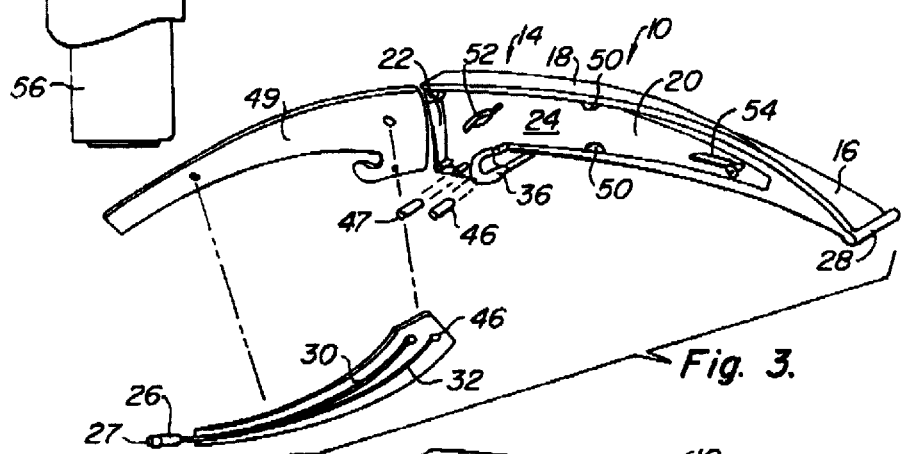
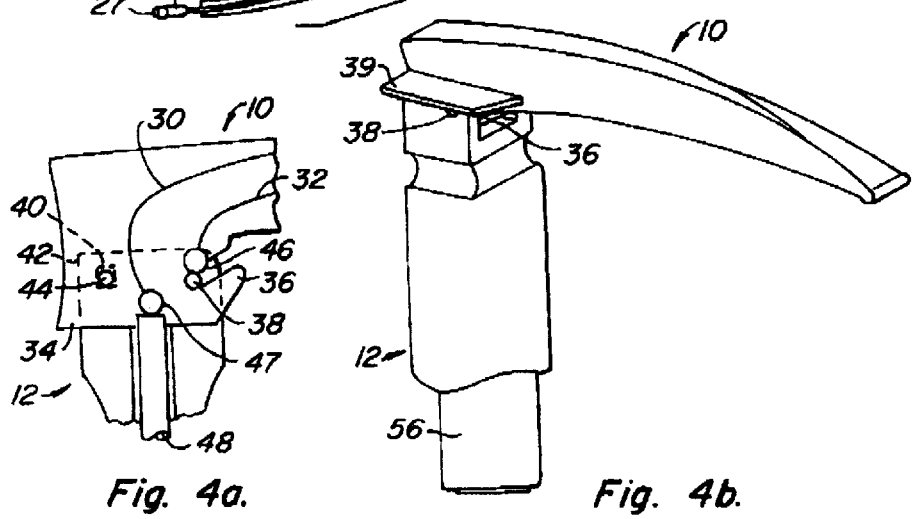

SINGLE USE LARYNGOSCOPE BLADE

This is a continuation of application Ser. No. 08/179,024, filed Jan. 7, 1994, now abandoned.

The present invention relates to laryngoscopes. More particularly, the present invention relates to disposable plastic laryngoscope blades.

As is known and explained, e.g., in U.S. Pat. No. 3,766,909, a laryngoscope is a type of device for assisting in the observation of the oral cavity, particularly the laryngeal areas. This device is frequently employed by an anesthesiologist to aid in the placement of a tube into the larynx of a patient for the passage of anesthetising gas. In order to obtain accurate placement, the instrument must be capable of restraining the patient's tongue, while engaging the epiglottis to reveal the larynx for visual observation. The laryngoscope is also useful for general examination of the larynx. These functions are greatly aided by the use of a light source in association with the laryngoscope blade to produce localized illumination within the area to be examined.

Furthermore, as known and explained, e.g., in U.S. Pat. No. 4,557,256, laryngoscopes generally comprise a blade and a cooperating handle, which are connected together in a generally L-shaped configuration. The handle normally serves as an enclosure for one or more batteries which energize a light bulb secured adjacent to the blade and connected by wires or other electrical conducting means to the batteries in the handle. The switch for activating the light is usually positioned immediately adjacent to the light bulb and is operated by the blade when it is connected onto the handle. The light from the bulb passes through a clear light conductor to the distal end of the blade, to illuminate the patient's mouth and larynx during the examination thereof by medical personnel. The surface of the blade adjacent to the handle is used to press against the tongue and mandible of a patient in a supine position, in order to prevent the patient's tongue from obstructing the visual examination of the larynx.

While the instrument is useful for examining the larynx, the primary function of the laryngoscope is to expose the larynx in order to facilitate the insertion of an endotracheal tube. The surface of the laryngoscope blade adjacent the handle is urged against the tongue and mandible to expose the larynx in such procedures, and the opposite blade surface is positioned opposing the upper front teeth of the patient.

As more fully explained, e.g., in U.S. Pat. No. 4,878,486, when anesthetized, the human body tends to function somewhat irregularly. For instance, the air passageway may close up, and stomach acid may enter the lungs. To avoid such a situation and protect the lungs from stomach acid, an endotracheal tube is normally inserted into the patient's air passageway with the aid of a device which is typically used to examine the larynx, namely a laryngoscope. A conventional laryngoscope comprises a cylindrically-shaped handle or housing with a detachable, elongate blade. The blade is usually hingedly attached to the laryngoscope housing at a contact point, and has either a C-shaped or L-shaped lateral cross-sectional shape, with inside and outside surfaces. The outside surface is shaped to conform to the interior surfaces of the patient's throat, and to facilitate lifting the patient's tongue, upon insertion of the blade into the patient's mouth and throat. The inside surface of the blade defines a space which includes a guide surface, through which the physician can sight down into the patient's throat. The blade has a light located adjacent its outer end to assist in viewing the larynx, and a rounded tip to help move the epiglottis to facilitate the insertion of an endotracheal tube without undue trauma to the patient's throat.

In recent years, grave concerns have been expressed with regard to the cleaning and sterilizing of laryngoscopes, especially with respect to the blade portion which is inserted into patients' throats and often comes into contact with bodily fluids, including blood. Fears have been raised concerning both the possibility of cross-contamination between patients and the infection of medical staff handling the equipment. In hospital environments, laryngoscope blades are now beginning to be routinely sterilized by autoclaving and are no longer just wiped clean or immersed in a bactericidal solution. These procedures are requiring hospitals to greatly increase stocks of laryngoscope handles and blades to allow this rotation to take place. However, in ambulances or other emergency medical care situations, an acute problem remains. Often, relatively expensive equipment is thrown away or left at the site of accidents, as priority care is given to the patient and to his removal to a hospital rather than to sorting through blood-stained swabs and bandages to retrieve possibly contaminated equipment.

Accordingly, there was felt to be a demand in the medical field for disposable covers for laryngoscopes, or for disposable blades, and many recent patents have been directed to this problem. Thus, e.g., U.S. Pat. Nos. 3,426,749; 4,583,527; 4,579,108; 4,878,486; 4,884,558; 4,972,825 and 5,065,738 all attempt to solve the aforementioned sterility problem by providing disposable covers or sheaths for the standard laryngoscope blade.

Similarly, U.S. Pat. Nos. 3,826,248; 3,598,113; 3,766,909; 4,037,588; 4,406,280; 4,570,614; 4,565,187; 4,406,280 and 4,930,495 provide different types of disposable blades for use in laryngoscopy.

Despite the existence of these patents and their proposed solutions, 99% of the laryngoscopes used remain of the conventional figuration with a standard metal handle and metal blade.

After careful analysis of the products described in said patents and offered for sale on the market, it has now been determined by Applicant that there exist major drawbacks and deficiencies in each of said products, which could explain their non-acceptability in the marketplace.

Laryngoscopes are used in life-threatening situations where the intensity of light emitted from the blade is a critical factor in allowing doctors to carry out successful intubation in the minimum amount of time. The anesthetist must feel sure of the instrument in his hand. Disposable sheaths or covers not only remove light intensity, but add a non-rigid component to the laryngoscope blade.

Disposable blades found on the market today have a light source in the handle and use a light guide for transmitting light from the light source associated with the handle to a point near the distal end of the blade. This arrangement provides illumination in the range of less than 500 Lux, which is unacceptable to doctors and professionals used to the power of conventional metallic laryngoscopes.

In order to be acceptable, a disposable blade should be inexpensive. While many of the proposed blades are inexpensive in themselves, they are proposed for use in combination with a specially-designed handle. Thus, each of the aforementioned patents relating to disposable blades teaches the use thereof in conjunction with a handle specially designed to uniquely interconnect with the proposed blade.

This becomes especially important when it is recognized that currently International Standard ISO 7376-1 clearly defines the interrelationship of mechanical fit and electrical contact, thereby permitting interchangeability between handles of the hook-on type and the blades of different manufacturers. None of the disposable blades proposed in said patents and/or marketed today complies with said standard, nor do they provide solutions for the compliance of disposable blades therewith.

With the above state of the art in mind, according to the present invention there is now provided a disposable plastic laryngoscope blade, detachably connectable to a hook-on-type conventional metallic laryngoscope handle in conformity with International Standard ISO-7376-1; said blade comprising a rigid plastic housing having a lower, tongue-engaging flange section extending along the length thereof, an upper, teeth-engaging flange section, and web sections interconnecting the upper and lower flanges to form a hollow cavity; an electric bulb having a rating of about 2 to about 2.5 Volts and about 0.35 to about 0.5 Amperes, positioned within said cavity adjacent the distal end of said blade and having positive and negative electrode conductors extending therefrom; a proximal base end provided with hooks or fittings for engaging complementary handle hooks or fittings in compliance with ISO-7376-1, said proximal base being provided with a positive central contact positioned to press against a standard insulated central contact provided in said handle when attached thereto, and elevating into an operating position to maintain conductivity from a power source in said handle and ensure illumination of said bulb while in said engaged operating position; a first current-conducting means connecting said positive electrode conductor to said positive central contact and a second current-conducting means connecting said negative electric conductor with a metallic surface of said handle.

In a first preferred embodiment of the present invention, said first and second conducting means are printed metal paths on a non-conducting element.

In a second preferred embodiment of the present invention, said first and second conducting means are flexible metallic strips.

In said second preferred embodiment of the present invention, preferably at least said second metallic strip terminates at its proximal end in a conductive ring, sized to override and make electrical contact with a locking pin of said proximal base end.

The disposable blade of the present invention also preferably comprises frangible means provided in said proximal base end, which are configured to be damaged upon the disengagement of said blade from said handle, to prevent the reuse of said blade.

Preferably, said bulb is an incandescent, krypton or other gas-filled bulb, providing illumination of at least 650 Lux.

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a perspective view of a preferred embodiment of laryngoscope blade according to the invention;

FIG. 2 is a fragmented, perspective view of an ISO standard holder for a laryngoscope blade;

FIG. 3 is an exploded view of the blade seen in FIG. 1;

FIG. 4a is a detail view and FIG. 4b is a perspective view, of the blade and holder assembled ready for use;

Figure 5A:
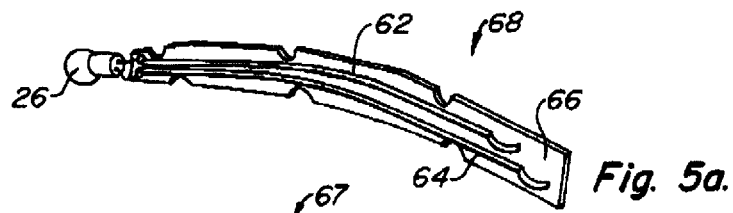
FIG. 5a is a perspective view showing the electrical conductors as a printed circuit.

There is seen in FIG. 1 a disposable plastic laryngoscope blade 10, detachably connectable to a hook-on type conventional metallic laryngoscope handle 12 in conformity with International Standard ISO-7376-1, which is seen in FIG. 2.

FIG. 1 shows the blade in ready-to-use form, and FIG. 3 shows the same blade 10 in exploded form, to reveal a preferred form of construction.

A rigid plastic housing 14 has a lower, tongue-engaging flange section 16 extending along the length thereof. An upper teeth-engaging flange section 18 is connected by web sections 20, 22 to the lower flange 16, to form a cavity 24.

The housing 14 can suitably be made of a tough thermoplastic such as ABS, acetal or polycarbonate. Polycarbonate is particularly advantageous, as it is available in transparent form, and the housing can be made therefrom without provision of a transparent window or aperture for the light bulb 26. ABS has safety advantages, in that it fails under excess stress in plastic yield instead of in brittle failure. Furthermore, it can be electroplated, to provide an appearance almost indistinguishable from a metal item.

FIG. 3 depicts an electric bulb 26, advantageously provided with a magnifying lens 27 and suitable for 2 to about 2.5 Volts, and drawing a current of about 0.35 to about 0.5 Amperes, positioned, when assembled, within the cavity 24 adjacent the distal end 28 of the blade 10. Preferably, bulb 26 is an incandescent bulb, providing illumination of at least 650 Lux, this level of illumination being acceptable to doctors accustomed to the power of conventional metallic laryngoscopes for visualization of the glottis.

In a further embodiment, the bulb 26 is a krypton or another type of gas-filled bulb, providing the same level of illumination, i.e., at least 650 Lux.

In a further embodiment, the bulb 26 is a tungsten wire filament-vacuum bulb providing a very high level of illumination, i.e., more than 900 Lux. In this case, the bulb has been so constructed that it has an operating life of only 5–10 minutes.

In all embodiments, positive and negative electrode conductors 30, 32 extend from the bulb 26.

A proximal base end 34 of blade 10 is provided with hooks 36 for engaging a complementary handle fitting, shown as a pin 38 in FIG. 2, in compliance with standard ISO-7376-1.

The blade 10 is provided with a locator shoulder 39, which provides positive location when abutting the handle fork 42, as seen in FIG. 4b.

In FIG. 2, a curved recess 40 is seen on an inner face of handle fork 42. The blade 10 is provided with a projection 44 seen in FIG. 4a, which enters the recess 40 and thereby secures blade 10 from inadvertent separation from the handle 12.

The second conductor 32 may be arranged to contact any metallic surface of the handle 12. Advantageously, the second metallic strip conductor 32 terminates at its proximal end in a conductive ring 46, best seen in FIG. 4a, sized to override and make electrical contact with the locking pin 38 securing the proximal base end 34 to the handle 12.

The electric circuit needed to power the bulb 26 is completed by a first current-conducting means 47, connecting the positive electrode conductor 30 to the positive central contact 48.

With regard to the particular form of construction of the blade 10 seen in FIG. 3, a cover plate 49 is configured to close the housing 14, attachment being to recesses 50. The housing 14 is provided with non-conducting separators 52, 54 configured to ensure that the conductors 30, 32 do not contact each other.

Referring again to FIG. 4a, it is seen that the base end 34 of the blade 10 is provided with a positive central contact 47 positioned to press against a standard insulated central contact 48 provided in the handle 12 when attached thereto as shown.

In FIG. 4b, the blade 10 is seen in an elevated operating position, where it maintains conductivity from a power source, a dry cell battery 56 in the shown embodiment, to ensure illumination of the bulb 26 while in said engaged operating position.

Shown in FIG. 5a are first and second conducting means 62, 64, which, in this embodiment, are printed metal paths on a non-conducting element 66. This circuit element 68 replaces the conductors 30, 32 seen in FIG. 3, and has cost advantages when manufactured in the large quantities required for a disposable blade.

Figure 5B:
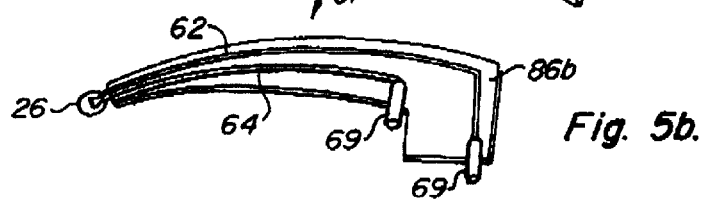
FIG. 5b is a perspective view showing similar electrical conductors terminating in connector tubes.

A further, similar circuit element 67 is seen in FIG. 5b. First and second conducting means 62, 64, printed on a non-conducting element 66b, each terminate in a conducting cylindrical terminal 69.

Figure 6:
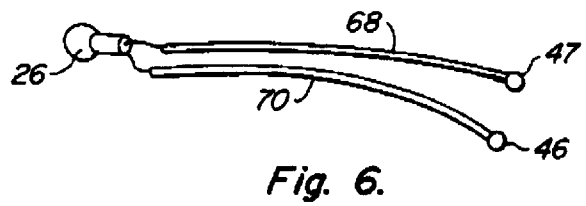
FIG. 6 is a perspective view showing the electrical conductors as metallic strips.

FIG. 6 shows an embodiment wherein the bulb 26 is connected to first and second conducting means, which are flexible metallic strips 68, 70 and which replace the conductors 30, 32 seen in FIG. 3. Such strips are more suitable when manufacture of moderate quantities is required.

Figure 7:
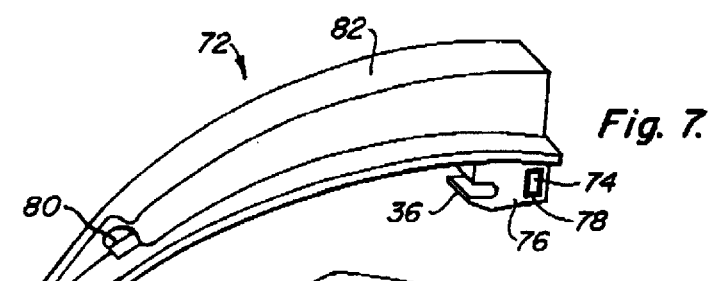
FIG. 7 is a perspective view of a final embodiment, provided with a frangible locking tongue.

A final embodiment of a blade 72 is shown in FIG. 7, further comprising frangible means 74 provided in the proximal base end 76. The means 74, shown in the form of a tongue provided with a break line 78, engages the recess 40, seen in FIG. 2, upon assembly of the blade 74 to handle 12, and is configured to break off, or at least to be damaged, upon the disengagement of the blade 72 from said handle, thereby discouraging the reuse of blade 72.

A shield 80 for protection of the electric bulb is made of a transparent material, and therefore the housing 82 may be made of an opaque plastic.

Figure 8:
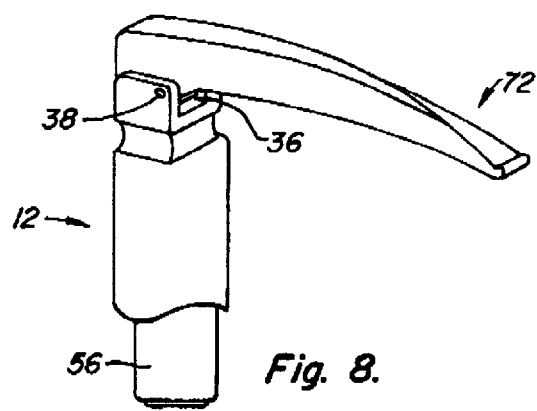
FIG. 8 is a perspective view showing the embodiment of FIG. 7 assembled to a handle.

FIG. 8 shows the blade 72 assembled to the handle 12. In this view it is seen that, unlike the blade 10, the blade 72 locates in the holder 12 using the means 74, and so does not require a locator shoulder; however, it still locks into a standard handle 12 which conforms to ISO 7376-1.

It will be evident to those skilled in the art that the invention is not limited to the details of the foregoing illustrated embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. In a hook-on-type conventional laryngoscope of the type having a conventional metallic handle in conformity with International Standard ISO-7376-1 which corresponds to ASTM Standard F 965-85 in which the handle hook-on fitting has a hinge pin to accept the hook-on fitting of a laryngoscope blade that is detachably connectable to said metallic handle; the improvement comprising a disposable plastic laryngoscope blade comprising:

a rigid plastic housing having a lower, tongue-engaging flange section extending along the length thereof, an upper, teeth-engaging flange section, and web sections interconnecting the upper and lower flanges to form an elongate hollow cavity; an electric bulb having a rating of about 2 to about 2.5 Volts and about 0.35 to about 0.5 Amperes, positioned within said cavity adjacent the distal end of said blade and having a first or positive and a second or negative electrical conductor extending therefrom; and a proximal base end provided with a hook-on fitting for engaging the complementary handle hook-on fitting in compliance with ISO-7376-1 and ASTM Standard F 965, said proximal base end being provided with a positive central contact positioned to press against an insulated central contact provided in the handle when attached thereto, wherein the blade is movable into an operating position to create and maintain a circuit including a power source in the handle to ensure illumination of said bulb while in said engaged operating position, the first positive current-conducting means passing through the cavity and connecting said first or positive electrical conductor to said positive central contact and a second current-conducting means passing through the cavity and connecting said negative electrical conductor with a metallic surface of the handle.

2. A disposable plastic laryngoscope blade according to claim 1, wherein said first and second conductors are printed metal paths on a non-conducting element.

3. A disposable plastic laryngoscope blade according to claim 1, wherein said first and second conductors are flexible metallic strips.

4. A disposable plastic laryngoscope blade according to claim 1, wherein at least said second metallic strip terminates at its proximal end in a conductive ring, the conductive ring being sized to make physical and electrical contact with the hinge pin of the handle.

5. A disposable plastic laryngoscope blade according to claim 1, further comprising frangible means provided in said proximal base end, which are configured to be damaged upon the disengagement of said blade from the handle, to prevent the reuse of said blade.

6. A disposable plastic laryngoscope blade according to claim 1, wherein said bulb is an incandescent bulb providing illumination of at least 650 Lux.

7. A disposable plastic laryngoscope blade according to claim 1, wherein said bulb is a krypton or another gas-filled bulb, providing illumination of at least 650 Lux.

8. A disposable plastic laryngoscope blade according to claim 1, wherein said bulb has been constructed to have an operating life of less than 10 minutes, thereby causing the blade to be of single use.

9. A disposable plastic laryngoscope blade according to claim 1 wherein said second electrical conductor terminates at its proximal end in a loop to make physical and electrical contact with the hinge pin of the handle.

10. A disposable plastic laryngoscope blade according to claim 1 wherein said first and second conductors are wires.

11. A disposable plastic laryngoscope blade for use in combination with and being detachably connectable to a hook-on-type conventional laryngoscope handle in conformity with International Standard ISO-7376-1 which corresponds to ASTM Standard F 965 in which the handle hook-on fitting has a hinge pin to accept the hook-on fitting of a laryngoscope blade, said disposable plastic laryngoscope blade comprising:

a rigid plastic housing having a lower, tongue-engaging flange section extending along the length thereof, an upper, teeth-engaging flange section, and a web section interconnecting the upper and lower flanges to form an elongated hollow cavity;

an electric bulb having a rating of about 2 to about 2.5 volts and about 0.35 to about 0.5 Amperes, positioned within said cavity adjacent the distal end of said blade and having a first or positive and a second or negative electrical conductor extending therefrom;

a proximal base end provided with a hook-on fitting for engaging the complementary handle hook-on fitting in compliance with ISO-7376-1 and ASTM Standard F 965, said proximal base end being provided with a positive central contact positioned to press against a standard insulated central contact in the handle when the blade is attached thereto;

the blade being movable on the hinge pin into an operating position to create and maintain a circuit that includes a power source in the handle to ensure illumination of said bulb while in said operating position;

a first current-conducting means passing through the cavity and connecting said first or positive electrical conductor to said positive central contact; and a second current-conducting means passing through the cavity and connecting said negative electrical conductor width a metallic surface of the handle.

* * * * *